US00PP10768P

United States Patent [19]

Rusinski

[11] Patent Number: Plant 10,768

[45] Date of Patent: Jan. 26, 1999

[54] ANTHURIUM PLANT NAMED 'DOLORES'

[76] Inventor: Gerd Rusinski, Aspisheimer Weg 19, 55459 Grolsheim, Germany

[21] Appl. No.: 818,835

[22] Filed: Mar. 14, 1997

[51] Int. Cl.[6] ..... A01H 5/00

[52] U.S. Cl. ..... Plt./88.1

[58] Field of Search ..... Plt./88.1

*Primary Examiner*—James R. Feyrer
*Assistant Examiner*—Melissa L. Kimball
*Attorney, Agent, or Firm*—C. A. Whealy

[57] ABSTRACT

A distinct cultivar of Anthurium plant named 'Dolores', characterized by its relatively compact growth habit; strong petioles and peduncles; flowers positioned above the foliage; early flowering; large, flat, rounded, smooth, and dark red flower spathes; and good post-production longevity.

3 Drawing Sheets

1

The present invention relates to a new and distinct cultivar of Anthurium plant, botanically known as *Anthurium scherzerianum,* and hereinafter referred to by the cultivar name Dolores.

The new cultivar is a product of a planned selection program conducted by the inventor in Grolsheim, Germany. The new cultivar is the result of 30 years of selection from nonpatented proprietary *Anthurium scherzerianum* selections. The cultivar Dolores was discovered and selected in the spring of 1992 by the inventor in a controlled environment in Grolsheim, Germany. This new Anthurium was selected on the basis of its relatively compact growth habit, flowers positioned above the foliage, rounded flower spathes, early flowering, dark red spathe color, and strong petioles and peduncles.

Asexual propagation of the new cultivar by division at Rhede, Germany, has shown that the unique features of this new Anthurium plant are stable and reproduced true to type in successive generations of asexual propagation.

The new Anthurium has not been observed under all possible environmental conditions. The phenotype may vary somewhat with variations in environment such as temperature and light intensity, without, however, any variance in genotype. The following observations, measurements and comparisons describe plants grown in Grolsheim, Germany, in a glass-covered greenhouse with an average day temperature of 25° C. and an average night temperature of 19° C.

The following traits have been repeatedly observed and are determined to be the unique characteristics of 'Dolores'. These characteristics in combination distinguish 'Dolores' as a new and distinct cultivar:

1. Relatively compact growth habit.
2. Strong petioles and peduncles.
3. Flowers positioned above the foliage.
4. Early flowering.
5. Large, rounded, flat and dark red flower spathes.
6. Good post-production longevity.

The accompanying colored photographs illustrate the overall appearance of the new cultivar, showing the colors as true as it is reasonably possible to obtain in colored reproductions of this type.

The first photograph comprises a top perspective view of a typical potted plant of 'Dolores'.

The second photograph comprises a close-up view of a typical flower of 'Dolores'.

The third photograph comprises a close-up view of a typical leaf of 'Dolores'. Flower and foliage colors in the photographs may appear different from the actual colors due to light reflectance.

In the following description, color references are made to The Royal Horticultural Society Colour Chart except where general terms of ordinary dictionary significance are used.

2

The following observations and measurements describe plants grown in Grolsheim, Germany, under commercial practice in a glass-covered greenhouse with average day and night temperatures ranging from 18° to 20° C. and average light levels of 30,000 lux.

Botanical classification: *Anthurium scherzerianum* cultivar Dolores.

Parentage: Selection of nonpatented proprietary *Anthurium scherzerianum* selections.

Propagation: By division or by tissue culture.

*Time to initiate roots.*—About 21 days at 20°.

Plant description:

*Plant shape.*—Upright, inverted triangle.

*Growth habit.*—Erect when young, becoming outwardly arching as leaves develop. Relatively compact, appropriate for 10 to 13-cm containers.

*Plant height.*—35 to 40 cm from soil level to top of leaf plane.

*Plant vigor.*—Low.

*Growth rate.*—Slow.

*Crop time.*—Usually 15 to 16 months are required from planting a young tissue-cultured plantlet to a finished plant with a height of 35 to 40 cm.

*Foliage description: Quantity of leaves per finished plant:* 18 to 24. Leaf size: Length: 22 to 27 cm. Width: 9 to 12 cm. Leaf shape: Very narrowly cordate. Leaf apex: Acuminate. Leaf base: Cordate. Margin: Entire. Leaf texture: Leathery, smooth, glabrous, somewhat glossy. Leaf aspect: Horizontal to upwards. Leaf color: Young, upper surface: 146A. Young, lower surface: 147C. Mature, upper surface: 147A. Mature, lower surface: 147C. Venation, upper surface: Light green. Petiole: Length, primary shoot: 16 to 21 cm. Cross-section: Concave. Color: 146C. Geniculum: Light green.

Flower description:

*Flower arrangement.*—Spathe with spadix held clearly above the foliage. Flowers arise from leaf axils.

*Flowering season.*—Year-round, recurrent.

*Postproduction longevity.*—Spathe/spadix maintain good substance and color for 3 to 5 weeks. Spathe/spadix persistent.

*Quantity of flowers per spadix.*—150 to 200.

*Flower size.*—1 to 2 mm.

*Flower shape.*—Rounded.

*Spathe.*—Shape: Broadly cordate, rounded. Apex: Broadly acuminate. Base: Cordate to rounded. Margin: Entire. Texture: Somewhat glossy. Aspect: Slightly convex. Size: Length: 9 to 12 cm. Width: 9 to 12 cm. Color: Abaxial surface: 45A. Adaxial surface: 45A.

*Spadix.*—Cross section: Elliptic. Longitudinal axis: Recurved at apex, twisting towards base. Size: Length: 6 to 8 cm. Diameter: 6 to 8 mm. Color: Base: 40A. Mature: Reddish orange. Apex: Red.

*Peduncle.*—Aspect: Strong and erect. Length: 28 to 32 cm. Cross-section: Elliptic. Color: Dark green with strong anthocyanin, red coloration increasing at distal end.

*Reproductive organs.*—Androecium: Pollen color: Cream white. Gynoecium: Stigma shape: Ovoid.

Disease resistance: No resistance nor susceptibility to disease has been noted under commercial production conditions.

Seed development: Seed development is rarely observed.

It is claimed:

1. A new and distinct cultivar of Anthurium plant named 'Dolores', as illustrated and described.

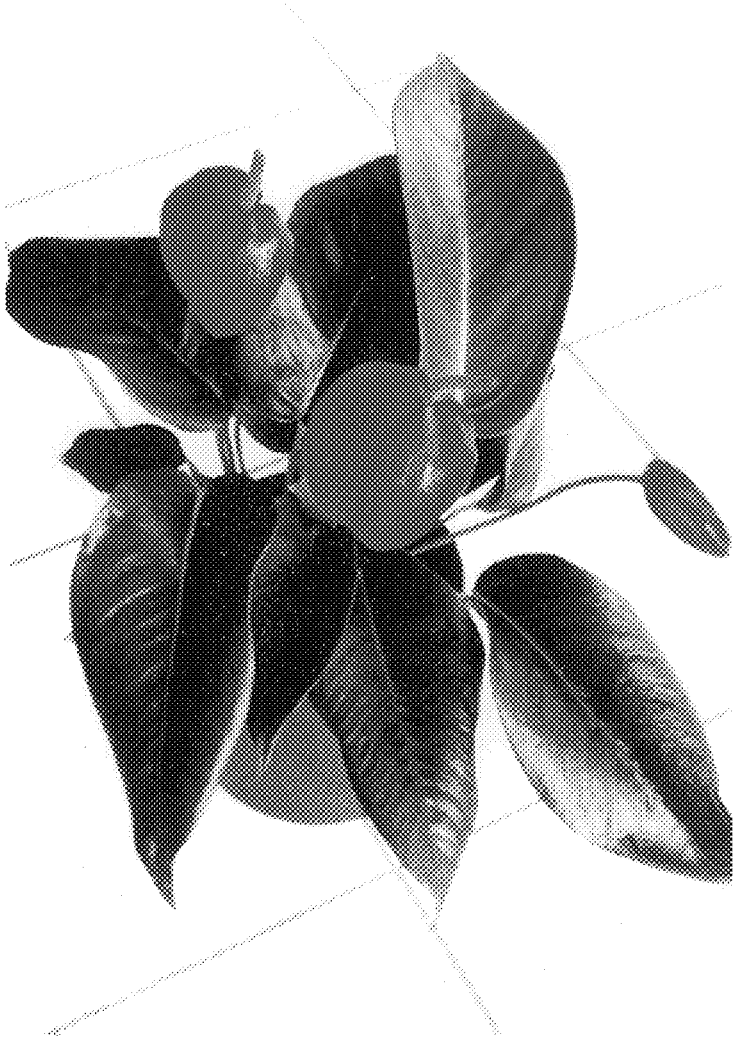

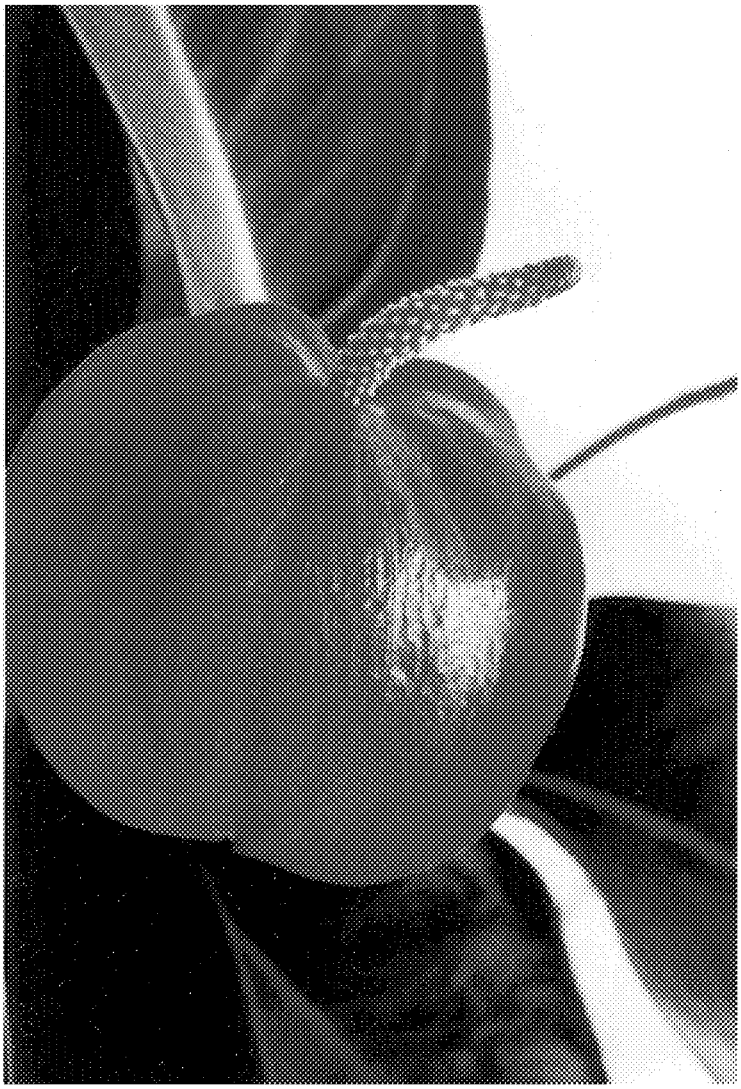

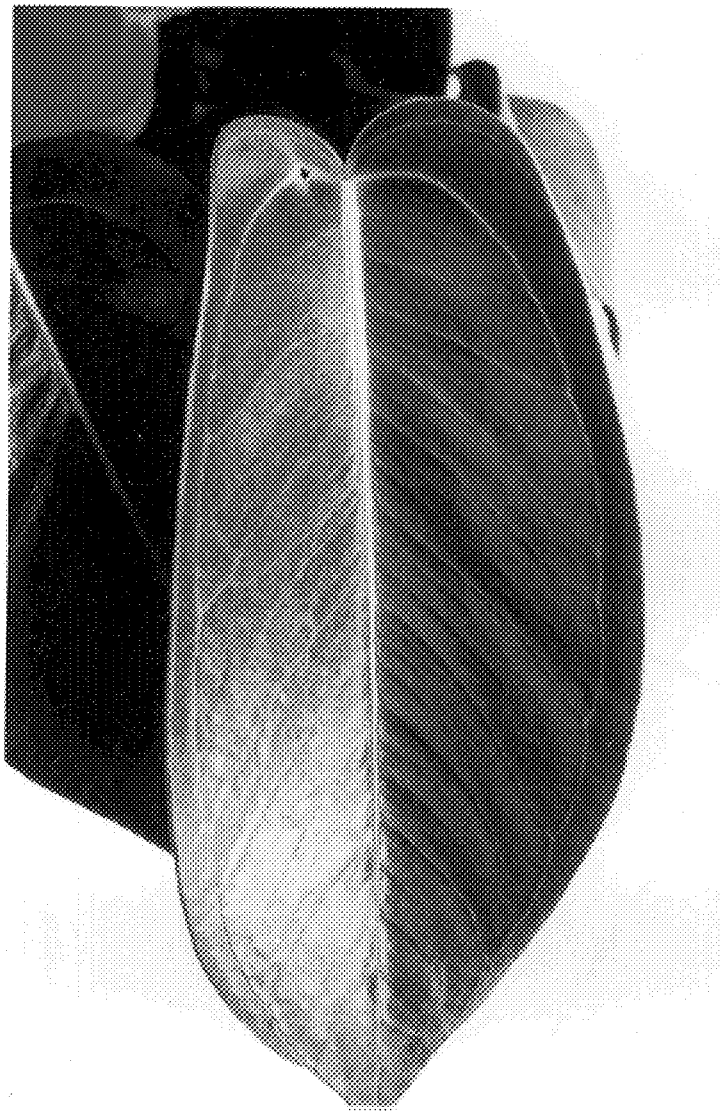

* * * * *